United States Patent [19]
Orth

[11] Patent Number: 5,874,520
[45] Date of Patent: Feb. 23, 1999

[54] PREPARATION OF NYLON SALTS FROM DIAMINE CARBAMATES AND DICARBOXYLIC ACIDS

[75] Inventor: John Harry Orth, Hockessin, Del.

[73] Assignee: E. I. du Pont de Nemours and Company, Wilmington, Del.

[21] Appl. No.: 929,717

[22] Filed: Sep. 15, 1997

Related U.S. Application Data

[60] Provisional application No. 60/032,557 Dec. 12, 1996.

[51] Int. Cl.$^6$ .......................... C08G 69/28; C07C 55/00; C07C 209/00
[52] U.S. Cl. .......................... 528/335; 562/590; 564/468
[58] Field of Search .......................... 562/590; 564/468; 528/335

[56] References Cited

U.S. PATENT DOCUMENTS 5,721,403  3/1998  Lang ....................................... 528/340

FOREIGN PATENT DOCUMENTS

0411790 A1  2/1991  European Pat. Off. ........ C08G 69/28
2257925  6/1974  Germany ........................ C07C 87/00
2638824  3/1978  Germany ........................ C07C 55/02

OTHER PUBLICATIONS

F. D. Snell et al., Polyamides, General, *Encyclopedia of Industrial Chemical Analysis*, 17, 275–276; 293–295; 303–305, 1973.

W. Gerhartz et al., Fibers, 4. Synthetic Organic, *Ullman's encyclopedia of industrial chemistry*, A10 567–579, 1987.

H. F. Mark et al., Polyamides, *Encyclopedia of polymer science and engineering*, 11, 360–365, 1988.

V. Hopp, Organic raw materials and large–scale products: Industrial processes, *Handbook of Applied Chemistry*, IV/8–20–21, 1983.

*Primary Examiner*—Samuel Barts
*Assistant Examiner*—Rosalynd Keys

[57] ABSTRACT

Substantially anhydrous nylon salts are made in a solid state process in which solid diamine carbamates are contacted and mixed with solid dicarboxylic acids in a near instantaneous reaction to produce the salt, and preferably are prepared by mixing the solid diamine carbamates and the solid dicarboxylic acids under conditions of high shear.

9 Claims, No Drawings

PREPARATION OF NYLON SALTS FROM DIAMINE CARBAMATES AND DICARBOXYLIC ACIDS

This application claims the benefit of U.S. Provisional Application No. 60/032,557, filed Dec. 12, 1996.

BACKGROUND OF THE INVENTION

The present invention relates to the preparation of nylon salts from diamine carbamates and dicarboxylic acids. More particularly, the invention relates to a solid state process for making nylon salts by contacting a diamine carbamate and a dicarboxylic acid.

Poly(hexamethylene adipamide), commonly known as "nylon 6,6," is typically manufactured commercially by first making an aqueous salt solution from its monomers, hexamethylene diamine and adipic acid. The commercial diamine, which is generally about 85% by weight diamine and about 15% by weight water, is mixed with additional water so that the resulting hexamethylene diammonium adipate (nylon 6,6 salt) solution usually contains water in the range of about 50% by weight. This solution is then used as a starting material and initial reaction medium for the solution/melt polymerization of nylon 6,6.

Techniques are known for obtaining a nylon salt from the solution. One such technique comprises adding an organic liquid (e.g., isopropanol) in which the salt is not soluble, or only slightly soluble (i.e., a non-solvent for the salt). The addition of the non-solvent will cause the salt to precipitate. The salt is then recovered and dried. In this technique, however, not only must the precipitated salt be recovered, but also the organic liquid itself must be recovered. Instead of precipitating the salt, another technique to obtaining dry salt is to heat the solution and evaporate the water. However, both of these techniques require the use of additional energy and/or additional process steps and can be time consuming and costly.

The direct formation of the dry salt avoids this expense and complexity. See generally H. F. Mark, et al., *Encyclopedia of Polymer Science and Technology*, Vol. 11, John Wiley & Sons, Inc., New York, 1988, p. 362, and V. Hopp, et al., *Handbook of Applied Chemistry*, Hemisphere Publishing Corp., Washington, D.C., 1983, pp. IV/8–20, 8–21.

SUMMARY OF THE INVENTION

This invention provides a solid state process for preparing a diamine/dicarboxylic acid salt, comprising contacting a solid diamine carbamate with a solid dicarboxylic acid.

In another embodiment, the invention provides a solid state process for preparing a substantially anhydrous diamine/dicarboxylic acid salt, comprising contacting a solid diamine carbamate with a solid dicarboxylic acid.

In yet another embodiment, the invention provides a solid state process for preparing a diamine/dicarboxylic acid salt, comprising contacting a solid diamine carbamate with a solid dicarboxylic acid under conditions of high shear.

These and other features of the invention will become apparent to those skilled in the art upon a further reading of this specification and the appended claims.

DETAILED DESCRIPTION OF THE EMBODIMENTS

Generally speaking, the present invention is based upon the discovery that by contacting a solid diamine carbamate with a solid dicarboxylic acid, an instantaneous reaction occurs at the surface of the contact and results in the formation of a diamine/dicarboxylic acid salt. No external energy is needed to drive the reaction.

The primary reaction which takes place according to the invention may be summarized as follows:

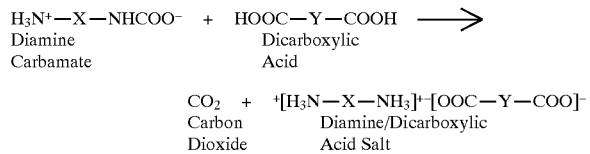

where X and Y each independently represent an aliphatic, alicyclic or aromatic group.

The present invention is further based on the discovery that the reaction between the solid diamine carbamate and the solid dicarboxylic acid is a surface chemistry phenomenon, which means that the reaction will continue until all of the available molecules on the surface of the contacting particles have reacted. The reaction can thus be continued by removing the salt formed at the particle-particle interface (such as by frictional rubbing or the like) to reveal "fresh" particle surfaces having unreacted molecules.

Any of a wide variety of diamine/dicarboxylic acid salts may be made by this process. Typically, such diamine/dicarboxylic acid salts which may be useful as starting materials for the manufacture of polyamides are those made from aliphatic or alicyclic diamines, and aliphatic or alicyclic diacid monomers. In addition, the invention is also useful to make salts for polyamide manufacture which have diamine or diacid components which are aromatic. Possible aromatic diamines are, for example, isophenylene diamine and paraphenylene diamine. Possible aromatic diacids are, for example, isophthalic acid and terephthalic acid.

The salts can be useful for the manufacture of homopolyamides where only one diamine and one diacid are used. Salts can also be made using the invention where a mixture of two or more diamines is reacted with one or a mixture of diacids or where a mixture of two or more diacids is reacted with one or a mixture of diamines. Aminocarboxylic acids, e.g., aminocaproic acid (the nylon 6 monomer unit), are also used in copolyamides. Minor quantities of one or more such aminocarboxylic acids, can be added to the reaction mixture also. If desired, small quantities of branching agents such as tris(2-aminoethyl)amine can also be incorporated into the resulting salt by addition to the reaction mixture.

Depending on the end use of the salt, the relative molar quantities of the diamine carbamate and dicarboxylic acid added to the reaction mixture can be adjusted as desired. For example, additional diamine can be incorporated into a salt for the manufacture of a polyamide used for fiber manufacture in which increased dyeability using anionic dyes is desired.

The invention is advantageously used to make salts for polyamides which are primarily aliphatic or alicyclic in character, e.g., less than 85% of the amide linkages of the resulting polymer are attached to two aromatic rings. Such polyamides are commonly referred to as nylons and are usually melt-processable. Such polyamides include those made from aliphatic diacids and aliphatic diamines such as poly(hexamethylene adipamide) ("nylon 6,6") and poly(butylene adipamide) ("nylon 4,6") and their copolymers. A particularly preferred salt is made from the reaction of 6-aminohexylcarbamic acid and adipic acid and is referred to as nylon 6,6 salt in the examples.

In the broadest sense, the invention comprises contacting a solid diamine carbamate with a solid dicarboxylic acid to produce a diamine/dicarboxylic acid salt. As used herein, "contacting" means a coming together or touching of the materials. The formation of the salt at the interface of the contacting surfaces of the solids is instantaneous. Because the reaction will stop once all of the available molecules at the surface interface have been reacted, the yields in this embodiment will generally be low. Yields can be improved by using smaller particles of the carbamate and the acid, which effectively increases the surface area (and thus the available reaction sites) relative to larger particles.

To further increase yields, it is preferred to react the diamine carbamate particles and the dicarboxylic acid particles with agitation. The agitation causes the salt formed at the interface of the contacting particles to be stripped away, thus revealing "fresh" surfaces which may then react further. The agitation will preferably be vigorous agitation under conditions of high shear, e.g., by grinding the particles using mills such as blade mills, attritors and the like. Yields are increased as the degree of agitation is increased and are maximized under high shear conditions. This is believed to be due not only to the stripping of the salt from the particle-particle contact interface, but also because the grinding action causes the carbamate and dicarboxylic acid particles to break apart, thus revealing additional reactive surfaces.

As noted above, the use of smaller particles will, in theory, increase the effective surface area and thus increase the efficiency of the process. In practice, however, the nature of the starting solids and the instantaneous nature of the reaction means that particle size is not particularly critical, particularly if a grinding apparatus is utilized, as long as the particles are small enough to allow for intimate mixing and grinding through the process. Total grinding times of 1–3 minutes, as set forth in the examples, are generally sufficient to cause a near complete reaction of the starting materials. Thus, as a practical matter, the use of starting materials in ultra-fine powder form would not be expected to appreciably decrease the grinding time or the process efficiency. Generally, particle sizes in the range of 50–400 μm are adequate. Measurements of particle size may be made on commercially available instruments, e.g., Coulter Multisizer, Coulter Corp., Hialeah, Fla.

The reaction between the diamine carbamate and the dicarboxylic acid may be exothermic. In theory, the reaction may prove so exothermic that the melting point of the starting materials, intermediates, or the product may be exceeded in the reaction vessel. In practice, however, the grinding times necessary to complete the reaction are generally short enough that the exothermic nature of the reaction, if any, should not create any difficulties. Accordingly, it will generally be satisfactory to carry out the reaction under ambient conditions. However, in some cases it may be necessary to carry the reaction out under cryogenic conditions or using cryogenic media (e.g., particulate dry ice or liquid nitrogen) when desirable or necessary to control the heat of the reaction. Moreover, the use of cryogenic conditions may be necessary to maintain the reacting materials in a solid state. One disadvantage to using cryogenic media is that they may allow moisture to be drawn from the ambient air, which in turn may decompose some of the carbamate salt.

The salts produced according to the process of this invention are substantially anhydrous and thus are particularly advantageous for use as a starting material for the manufacture of polyamides such as nylon 6,6. By "substantially anhydrous" we mean that the salt generally contains no more than about 5% by weight water and preferably no more than 1% by weight water. The salt is recovered from the process as a stable, free-flowing powder which can be easily shipped for use at remote locations. After dissolution in water, the salts can be used to make conventional aqueous solutions containing about 50% water by weight for use in common commercial processes for the manufacture of polyamide polymers. For the manufacture of nylon 6,6, the salt produced by the invention is less dangerous than the ~85% hexamethylene diamine solution which is a typical form for shipping the diamine to keep it in the liquid state at moderate temperatures.

The diamine carbamates used in the practice of this invention may be prepared by known methods, such as the method disclosed in U.S. Pat. No. 4,102,801. To further improve the ease and efficiency of the present process, the diamine carbamate may be prepared by reacting solid carbon dioxide with solid diamine under conditions of high shear as noted above. The solid dicarboxylic acid can then be added directly to the mixing vessel and the agitation continued for a brief period to form the diamine/carboxylic acid salt.

EXAMPLES

The following examples are intended to illustrate the invention without limiting the invention to the embodiments described. Percentages are by weight unless otherwise indicated.

Infrared (IR) spectrometry was performed using standard Fourier Transform-Infrared (FT-IR) microscopic techniques with using an ANALECT AQS-20 Spectrometer with an AQM-515 Infrared Microscope Module (KVB-ANALECT, Irvine, Calif. 92718). Melting points were obtained using a capillary melt apparatus (cat. no. 6406-K, Thomas Hoover, available from Arthur H. Thomas, Swedesboro, N.J.).

The following abbreviations are used in the examples below:

DIAK No. 1=6-aminohexylcarbamic acid (CAS 143-06-6), DuPont, Wilmington, Del.; HMD=hexamethylenediamine.

Example 1

On a bed of dry ice in a single-bladed laboratory mixer (Chemical Rubber Co., Cleveland, Ohio) were placed 3.6515 g of adipic acid (0.0250 moles) and 3.9902 g DIAK No. 1 (0.0249 moles), which were then allowed to cool for one minute and then ground/mixed for one minute. An IR spectrum of the resulting white powder indicated that the sample was a mixture of adipic acid, hexamethylenediamine carbamate salt and nylon 6,6 salt. Approximately 24% of the reactants had reacted to form the nylon 6,6 salt.

Example 2

Into a single-bladed laboratory mixer were placed 3.6503 g of adipic acid (0.0250 moles) and 4.0140 g DIAK No. 1 (0.0251 moles), which were then ground/mixed for one minute. No cryogen was used. An IR spectrum of the resulting white powder indicated that the sample was mostly nylon 6,6 salt, with small amounts of residual adipic acid and HMD carbamate salt. Approximately 90% of the reactants had reacted to form the nylon 6,6 salt.

Example 3

Into a single-bladed laboratory mixer were placed 3.65 g of adipic acid (0.0250 moles) and 4.00 g DIAK No. 1

(0.0251 moles), which were then ground/mixed. No cryogen was used. Samples were removed after 1 minute, 3 minutes and 5 minutes grinding time for analysis. IR spectra indicated that after 1 minute of grinding the sample was mostly nylon 6,6 salt (roughly 80%), with a small amount of residual HMD carbamate salt and no evidence of residual adipic acid. After 3 minutes and 5 minutes of grinding, the IR spectra matched that of nylon 6,6 salt and showed no evidence of residual reactants.

Example 4

Adipic acid and DIAK No. 1 were separately ground with dry ice in a single-bladed laboratory mixer to reduce particle size, then allowed to dry over a weekend. The use of cryogen caused the samples to absorb water from the humid laboratory air and agglomerate. A 3.0 g sample of the pre-ground adipic acid (0.0205 mole) and 3.3 g of the pre-ground DIAK No. 1 (0.0206 mole) were placed into the laboratory mixer and ground. No cryogen was used. Samples were removed after 1 minute, 3 minutes and 5 minutes grinding time for analysis. After 1 minute of grinding, the sample was mostly nylon 6,6 salt (roughly 82%) with some residual HMD carbamate and melted at 160°–190° C. After 3 minutes of grinding, the sample was approximately 92% nylon salt and melted at 196°–200° C. The residual HMD carbamate was approximately half that from the sample ground for 1 minute. After 5 minutes of grinding, the sample melted at 196°–200° C., and was still approximately 92% nylon salt. There was no evidence of residual adipic acid in any of the three samples.

What is claimed is:

1. A solid state process for preparing a diamine/dicarboxylic acid salt, comprising contacting with agitation a solid diamine carbamate with a solid dicarboxylic acid.

2. The process of claim 1, wherein contacting the solid diamine carbamate with the solid dicarboxylic acid further comprises mixing under conditions of high shear.

3. The process of claim 1, wherein contacting the solid diamine carbamate with the solid dicarboxylic acid is conducted under cryogenic conditions.

4. The process of claim 3, wherein the cryogenic conditions comprises mixing the solid diamine carbamate with the solid dicarboxylic acid in the presence of dry ice particles.

5. The process of claim 3, wherein the cryogenic conditions comprises mixing the solid diamine carbamate with the solid dicarboxylic acid in the presence of liquid nitrogen.

6. The process of claim 1, wherein said diamine carbamate comprises a carbamate of a diamine selected from the group consisting of aliphatic, alicyclic, and aromatic diamines having 2 to 16 carbon atoms.

7. The process of claim 1, wherein said dicarboxylic acid is selected from the group consisting of aliphatic, alicyclic, and aromatic dicarboxylic acids having 2 to 16 carbon atoms.

8. The process of claim 1, wherein said diamine carbamate is 6-aminohexylcarbamate and said dicarboxylic acid is adipic acid.

9. The process of claim 1, wherein the diamine/dicarboxylic acid salt is substantially anhydrous.

* * * * *